United States Patent
Kim et al.

US 8,702,608 B2
Apr. 22, 2014

(54) METHOD FOR ESTIMATING ACOUSTIC VELOCITY OF ULTRASONIC IMAGE AND ULTRASONIC DIAGNOSIS APPARATUS USING THE SAME

(75) Inventors: Gyu Won Kim, Gyunggi-do (KR); Ho Seop Jeong, Gyunggi-do (KR); Kyoung Joong Min, Seoul (KR)

(73) Assignee: Samsung Electro-Mechanics Co., Ltd., Gyunggi-Do (KR)

( * ) Notice: Subject to any disclaimer, the term of this patent is extended or adjusted under 35 U.S.C. 154(b) by 726 days.

(21) Appl. No.: 12/950,829

(22) Filed: Nov. 19, 2010

(65) Prior Publication Data
US 2012/0035482 A1    Feb. 9, 2012

(30) Foreign Application Priority Data

Aug. 5, 2010    (KR) ................. 10-2010-0075639

(51) Int. Cl.
*A61B 8/00*    (2006.01)
(52) U.S. Cl.
USPC ............ 600/437; 600/407; 600/441; 600/443
(58) Field of Classification Search
USPC .................. 600/407, 437, 441, 443
See application file for complete search history.

(56) References Cited

U.S. PATENT DOCUMENTS

| | | | |
|---|---|---|---|
| 5,638,820 A * | 6/1997 | Chen et al. ............ | 600/437 |
| 7,333,543 B2 * | 2/2008 | Choi .................. | 375/240.16 |
| 2004/0081340 A1 * | 4/2004 | Hashimoto .......... | 382/128 |
| 2006/0235302 A1 | 10/2006 | Grossman et al. | |
| 2008/0242999 A1 * | 10/2008 | Kakee .............. | 600/458 |

FOREIGN PATENT DOCUMENTS

EP    1 262 148 A1    12/2002

OTHER PUBLICATIONS

Office Action from counterpart German Patent Application No. 10-2010 051 620.1, mailed Jun. 3, 2011, 6 pages.

* cited by examiner

*Primary Examiner* — Joel Lamprecht
(74) *Attorney, Agent, or Firm* — Bracewell & Giuliani LLP; Brad Y. Chin

(57) ABSTRACT

Disclosed herein are a method for estimating acoustic velocity of an ultrasonic image and an ultrasonic diagnosis apparatus using the same. The method for estimating acoustic velocity of an ultrasonic image includes: (A) dividing each of the ultrasonic images into a plurality of blocks; (B) extracting contours of ultrasonic images for each block of one frame among the ultrasonic images; (C) calculating and analyzing average luminance values of each block; (D) determining the optimal block number using the average luminance values and selecting the optimal blocks; and (E) estimating and applying the real acoustic velocity, whereby the acoustic velocity is estimated in real time and is applied to the ultrasonic diagnosis apparatus.

9 Claims, 5 Drawing Sheets

METHOD FOR ESTIMATING ACOUSTIC VELOCITY OF ULTRASONIC IMAGE AND ULTRASONIC DIAGNOSIS APPARATUS USING THE SAME

CROSS REFERENCE TO RELATED APPLICATION

This application claims the benefit of Korean Patent Application No. 10-2010-0075639, filed on Aug. 5, 2010, entitled "Method For Estimating Acoustic Velocity Of Ultrasonic Image And Ultrasonic Diagnosis Apparatus Using the Same" which is hereby incorporated by reference in its entirety into this application.

BACKGROUND OF THE INVENTION

1. Technical Field

The present invention relates to a method for estimating acoustic velocity of an ultrasonic image and an ultrasonic diagnosis apparatus using the same.

2. Description of the Related Art

An ultrasonic diagnosis apparatus is one of the most important diagnosis apparatuses, which are being used in various fields. In particular, the ultrasonic diagnosis apparatus has been widely used in the medical field due to its noninvasive and nondestructive characteristics to objects. Recently, a high-performance ultrasonic system is used to generate 2-dimensional or 3-dimensional images of the inside of objects.

Generally, the ultrasonic diagnosis apparatus receives echo waves obtained by reflecting a part of the ultrasonic waves transmitted from an ultrasonic probe from a change point (change surface) of a tissue structure in an object and generates a tomographic image of an object based on the echo waves.

The generated ultrasonic image can be generated by propagating ultrasonic waves emitted from the ultrasonic probe to the tissue of the object and collecting reflected waves (echo waves) which are returned by being reflected from the tissue.

In the prior art, the ultrasonic diagnosis apparatus generates the ultrasonic images by operating the above-mentioned processes in order to diagnose the tissue in the human body. In this case, the ultrasonic diagnosis apparatus focuses beams under the assumption that the ultrasonic diagnosis apparatus has the same acoustic velocity (for example, about 1540 m/s) in all the regions of the tissue in the human body. However, the tissue in the human body has inherent acoustic velocity according to each vehicle.

For this reason, a difference between the real acoustic velocities of each tissue in the human body and the assumed acoustic velocities may be generated. The difference may have an effect on the reflected wave returned by being reflected from each tissue in the human body.

Therefore, as the difference between the real acoustic velocities in different types of tissue of the human body and the assumed acoustic velocities is increased, the difference between the reflected waves may also be increased. As a result, the beams reflected from the tissue in the human body become defocused, which causes a problem of degrading resolution and tissue contrast by distorting images.

Therefore, in order to obtain higher-definition ultrasonic images for a more accurate diagnosis, there is a need to more rapidly and accurately estimate the real acoustic velocities of each part of the human body and apply them to the ultrasonic diagnosis apparatus.

SUMMARY OF THE INVENTION

An aspect of the present invention is to provide a method for estimating acoustic velocity of an ultrasonic image in real time by dividing ultrasonic images and defining analysis regions of the divided images and an ultrasonic diagnosis apparatus using the same.

According to an embodiment of the present invention, there is provided a method for estimating acoustic velocity of an ultrasonic image, including: (A) dividing each of the ultrasonic images of a plurality of input frames into a plurality of blocks; (B) extracting contours of ultrasonic images corresponding to each block divided into a plurality of blocks for one frame among the ultrasonic images of the plurality of divided frames; (C) calculating and analyzing average luminance values of each block in order to select optimal blocks in a sequence of blocks having the maximum luminance value among average luminance values of each block when the contour extraction for each block is completed; (D) determining the optimal block number according to the average luminance of the analyzed frames by calculating the average luminance values of the analyzed frames using the average luminance values of each analyzed block and selecting the optimal blocks as many as the optimal block number; and (E) selecting, as the optimal frame, the frame corresponding to the optimal blocks having the maximum luminance value among the optimal blocks of each frame after comparing the selected optimal blocks with the optimal blocks of the remaining frames and estimating and applying the acoustic velocity of the optimal frame as the real acoustic velocity.

Step (B) extracts the contours of the ultrasonic images of each block by applying a difference image filter to each block to calculate the luminance values of each pixel for each block.

The difference image filter applied to each block calculates the absolute value of the difference of the luminance value between the pixels adjacent to one pixel to determine the maximum absolute value among the absolute values as the luminance value of the one pixel.

Step (C) calculates the average luminance values of each block by dividing the total sum of the luminance values of each pixel for each block by the total pixel number of each block.

Step (D) includes: (D-1) calculating the average luminance values of the analyzed frames by using the average luminance values of each analyzed block; (D-2) determining the optimal block number according to the average luminance values of the analyzed frames; and (D-3) selecting the optimal blocks as many as the determined optimal block number in an order of the maximum luminance value among the average luminance values of each block.

Step (D-1) calculates the average luminance values of the analyzed frames by dividing the total sum of the average luminance values of each analyzed block by the total block number of the analyzed frames.

Step (E) includes: (E-1) comparing the selected optimal blocks with the optimal blocks of the remaining frames; (E-2) selecting the frame corresponding to the optimal blocks having the maximum luminance values among the optimal blocks of each frame as the optimal frame; and (E-3) estimating and applying the acoustic velocity of the optimal frame as the real acoustic velocity.

According to an embodiment of the present invention, there is provided an ultrasonic diagnosis apparatus, including: an ultrasonic transmitter that generates transmitting signals according to a control signal and converts the transmitting signals into ultrasonic beams; an ultrasonic probe that emits the ultrasonic beams to objects and receives reflected waves returned from the objects; an ultrasonic receiver that converts the reflected wave into electric signals to generate the received signals; an image processor that divides and extracts the received signals into a plurality of acoustic velocities and generates the ultrasonic images of the plurality of frames; an acoustic velocity determining unit that divides ultrasonic images of one frame among the ultrasonic images of the plurality of frames generated from the image processor into the plurality of blocks to extract contours, analyzes the luminance values of each block to determine the optimal block number, and selects the optimal frame by selecting the optimal blocks as many as the optimal block number and applying them to the remaining frame to estimate the acoustic velocity of the optimal frame as the real acoustic velocity of the reflected wave; and a controller that performs a control to generate the ultrasonic image control signal, generate thee ultrasonic beam according to the control signal and receive the reflected wave of the emitted ultrasonic beam to generate the ultrasonic images of the plurality of frames, divide the ultrasonic image of one frame among the ultrasonic images of the plurality of generated ultrasonic images into a plurality of blocks to extract contours, analyze the luminance values of each block to determine the optimal block number, and select the optimal frame by selecting the optimal blocks as many as the optimal block number and applying them to the remaining frame to estimate the acoustic velocity of the optimal frame as the real acoustic velocity of the reflected wave.

The ultrasonic diagnosis apparatus further includes a data output unit outputting the ultrasonic images.

The image processor includes: an image extracting module that divides the received signals into the plurality of acoustic velocities to extract the plurality of image signals; and an image generating module that generates the ultrasonic images of the plurality of frames based on the plurality of images signals.

The acoustic velocity determining unit includes: an image dividing module that divides the ultrasonic images of one frame of the ultrasonic images of the plurality of frames generated from the image processor into the plurality of blocks; a contour extracting module that extracts the contours of the ultrasonic images of each block by applying the difference image filter to the ultrasonic images of each block of one of the plurality of frames to calculate the luminance values for each pixel of each block; an image analyzing module that calculates the average luminance values of each block to digitize and analyze the ultrasonic images of each block when the contour extraction of each block is completed; an image comparing module that determines the optimal block number according to the average luminance value of the analyzed frames to select the optimal blocks as many as the determined optimal block number in an order of the largest value among the average luminance values of each block and compares the optimal blocks of each frame by applying the positions of the optimal blocks to the remaining frames to select the optimal blocks having the maximum luminance value; and an acoustic velocity determining module that selects the frame corresponding to the optimal blocks having the maximum luminance values as the optimal frame to estimate the selected optimal frame as the real acoustic velocity of the reflected wave.

DESCRIPTION OF THE PREFERRED EMBODIMENTS

Figure 1:
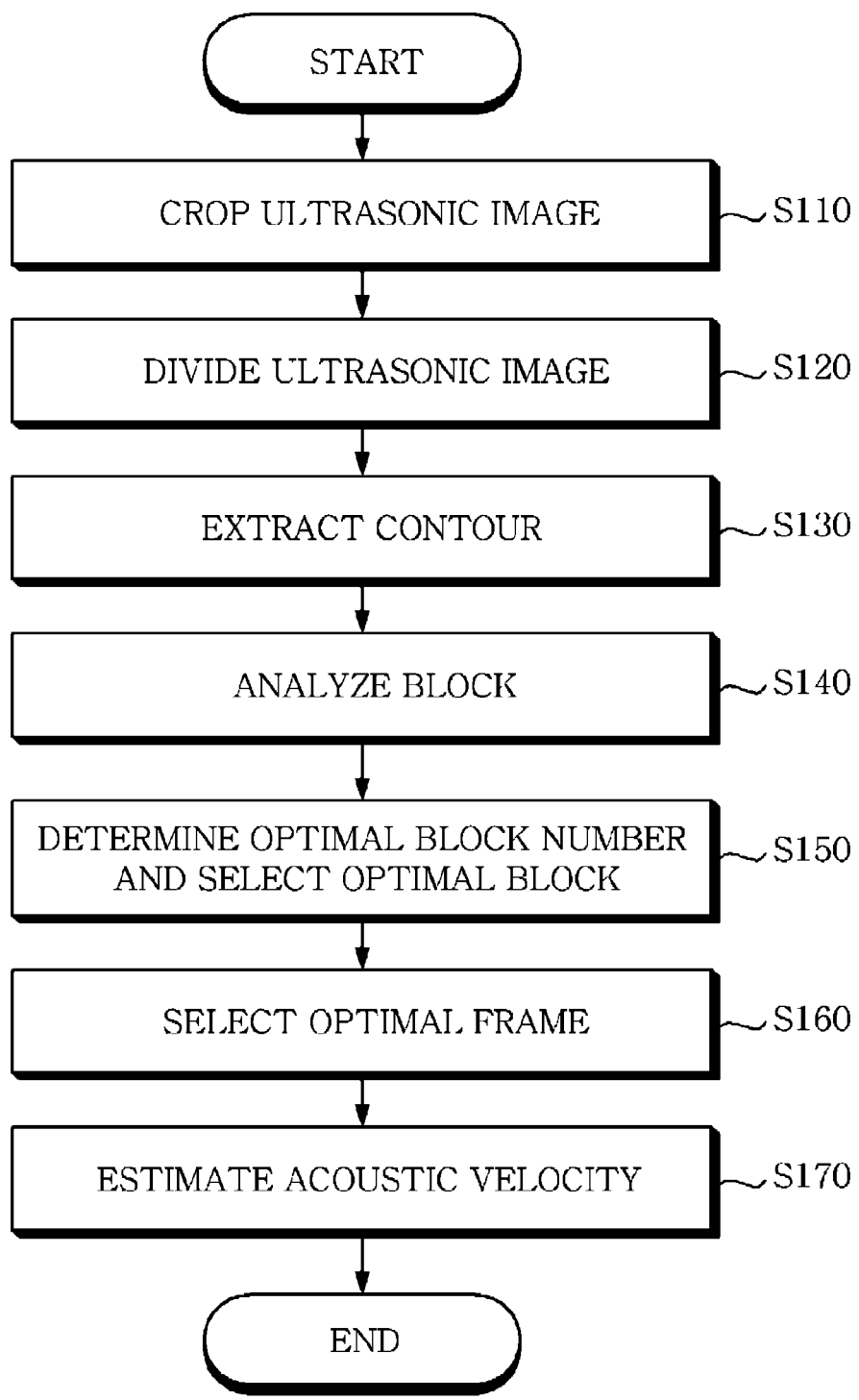
FIG. 1 is a flowchart schematically showing a method for estimating acoustic velocity of an ultrasonic image according to an embodiment of the present invention.

Various features and advantages of the present invention will be more obvious from the following description with reference to the accompanying drawings.

Terms or words used in the specification and claims herein should be not construed as a general and lexical meaning and should be construed as the meaning and concept meeting the technical idea of the present invention based on a principle that the present inventors can properly define the concepts of terms in order to elucidate their own invention in the best method.

The above and other objects, features and advantages of the present invention will be more clearly understood from the following detailed description taken in conjunction with the accompanying drawings. In the specification, in adding reference numerals to components throughout the drawings, it is to be noted that like reference numerals designate like components even though components are shown in different drawings. Further, when it is determined that the detailed description of the known art related to the present invention may obscure the gist of the present invention, the detailed description thereof will be omitted.

Hereinafter, preferred embodiments of the present invention will be described in detail with reference to the accompanying drawings.

In addition, for the convenience of explanation, in the present invention, it is assumed that acoustic velocities of ultrasonic waves emitted to objects are assumed to be 1400 m/s to 1590 m/s and received signals returned by being reflected therefrom are divided into 10 m/s to obtain ultrasonic images of 20 frames from 20 received signals.

Figure 2:
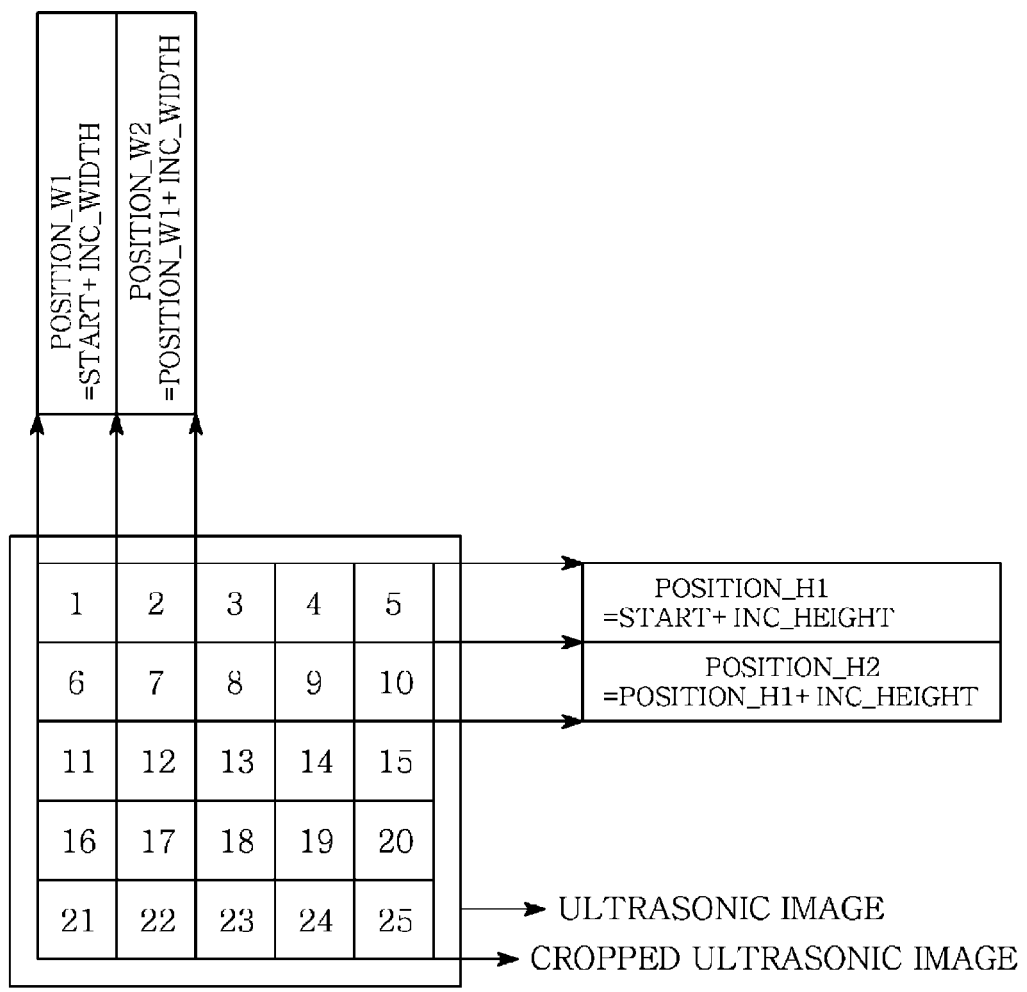
FIG. 2 is a diagram schematically showing a method for dividing ultrasonic images into a plurality of blocks according to an embodiment of the present invention.
Figures 3, 4:
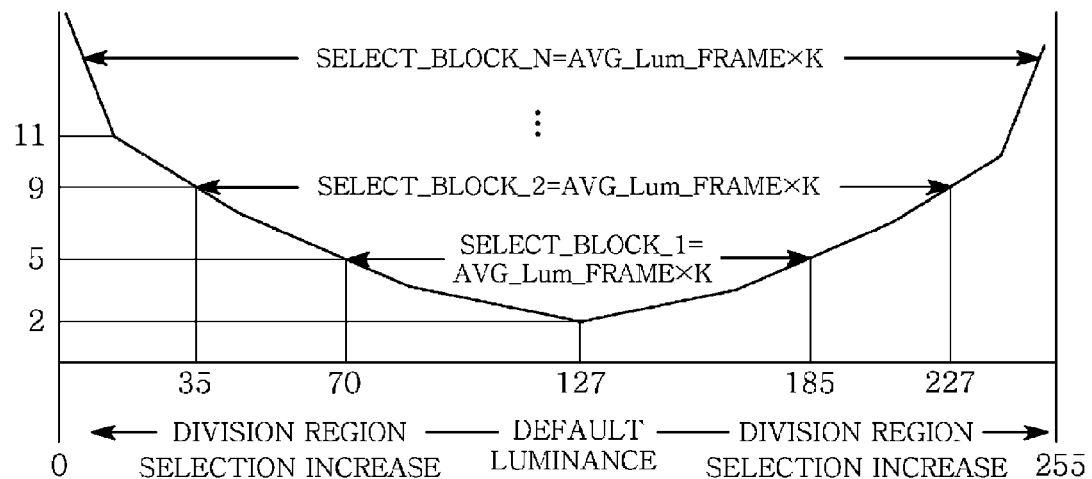
FIG. 3 is a diagram for explaining a difference image filter according to an embodiment of the present invention.
FIG. 4 is a diagram for explaining a method for determining the optimal block number according to an average luminance value of a frame according to an embodiment of the present invention.

FIG. 1 is a flowchart schematically showing a method for estimating acoustic velocity of an ultrasonic image according to an embodiment of the present invention, FIG. 2 is a diagram schematically showing a method for dividing ultrasonic images into a plurality of blocks according to an embodiment of the present invention, and FIG. 3 is a diagram for explaining a difference image filter according to an embodiment of the present invention.

Referring to FIG. 1, a method for estimating acoustic velocity of an ultrasonic image according to an exemplary of the present invention includes cropping ultrasonic images (S110), dividing the ultrasonic images (S120), extracting a contour (S130), analyzing blocks (S140), determining the optimal block number and selecting optimal blocks (S150), selecting optimal frame (S160), and estimating acoustic velocity (S170).

At the cropping the ultrasonic images (S110), the ultrasonic images are cropped to have a predetermined size.

The cropping the ultrasonic images is to primarily remove unnecessary portions when there are ultrasonic images in various shapes, including a fan shape and is similarly applied to the ultrasonic images of 20 frames.

In addition, the cropping the ultrasonic images (S110) may be configured to include a user mode and an automatic mode. For example, in the case of the user mode, a user directly sets portions to be cropped to manually crop them, seeing the displayed ultrasonic images, while in the case of the automatic mode, it automatically crops portions to be cropped by previously setting them at the time of design.

The cropped ultrasonic images are divided into a plurality of blocks (for example, N×M) at the dividing the ultrasonic images (S120).

The ultrasonic images cropped at step S110 are divided into N×M (for example, 5×5) blocks as shown in FIG. 2. For the convenience of explanation, each block is numbered.

In this case, the width and height of each block are calculated by the following Equations (1) and (2) at the time of dividing the cropped ultrasonic images.

$$INC\_W = R\_size/N \quad (1)$$

$$INC\_W = C\_size/M \quad (2)$$

In Equation (1), INC_W represents a width of each block, R_size is a width of the cropped ultrasonic images, and N represents the row block number.

In addition, in Equation (2), INC_H represents the heights of each block, C_size represents the heights of the cropped ultrasonic images, and M represents the column block number.

According to Equations (1) and (2), the widths of each block are calculated by dividing the widths of the cropped ultrasonic images by the row block number and the heights of each block are calculated by dividing the heights of the cropped ultrasonic images into the column block number.

Thereafter, the cropped ultrasonic images are divided into a plurality (for example, N×M) of blocks (for example, a plurality of rows and columns) by using the following Equations (3-1) to (3-m) and (4-1) to (4-n).

$$POSITION\_W1 = START + INC\_W \quad (3\text{-}1)$$

$$POSITION\_W2 = POSITION\_W1 + INC\_W \quad (3\text{-}2)$$

$$\vdots$$

$$POSITION\_Wm = POSITION\_Wm-1 + INC\_W \quad (3\text{-}m)$$

Equations (3-1) to (3-m) are equations calculating column positions of each block that are to be divided so as to divide the cropped ultrasonic images into M column blocks.

$$POSITION\_H1 = START + INC\_H \quad (4\text{-}1)$$

$$POSITION\_H2 = POSITION\_H1 + INC\_H \quad (4\text{-}2)$$

$$\vdots$$

$$POSITION\_Hn = POSITION\_Hn-1 + INC\_H \quad (4\text{-}n)$$

Equations (4-1) to (4-m) are equations calculating column positions of each block that are to be divided so as to divide the cropped ultrasonic images into N row blocks.

Referring to FIG. 2, as represented by Equations (3-1) to (3-m) and (4-1) to (4-n), the cropped ultrasonic images are divided into a plurality of blocks in such a manner that in the row positions and column positions of each block, a division position POSITION_W1 and POSITION_H1 of a row and a column of a first block (block 1) is calculated by adding a height INC_H and a width INC_W of each block calculated by Equations (1) and (2) to START and in order to obtain a division position of a row and a column of the subsequent block (for example, block 2 or block 6), a second division position POSITION_W2 and POSITION_H1 is calculated by again adding the height INC_H and the width INC_W of each block to the calculated division positions POSITION_W1 and POSITION_H1.

Further, step S120 is similarly applied to the ultrasonic images of 20 frames.

Each block divided into a plurality of blocks at step S120 extracts contours of the ultrasonic images corresponding to each block at the extracting the contours (S130).

In this case, in order to extract the contours of the ultrasonic images corresponding to each block, a difference image filter of L×L pixels (for example, 3×3 pixel) is used, which is shown in FIG. 3.

Referring to FIG. 3, the difference image filter of 3×3 pixels is used and for the convenience of explanation, a sign is affixed to each pixel.

In the difference image filter of the 3×3 pixels, a luminance value of a pixel R is set to a maximum value among the absolute values of luminance difference of pixels P1 to P9 adjacent to the pixel R.

For example, the absolute values of the luminance difference between the pixels P1 to P9 adjacent to the pixel R may be obtained according to the following Equations (5) to (7).

$$\text{Absolute value 1} = |\text{Luminance value of } P1 - \text{Luminance value of } P9| \quad (5)$$

$$\text{Absolute value 2} = |\text{Luminance value of } P4 - \text{Luminance value of } P6| \quad (6)$$

$$\text{Absolute value 3} = |\text{Luminance value of } P2 - \text{Luminance value of } P8| \quad (7)$$

The largest value among the calculated absolute value 1, absolute value 2, and absolute value 3 becomes the luminance value of the pixel R.

When the difference image filter of the 3×3 pixels is applied to all the pixels of block 1 according to the foregoing manner, the luminance values of each pixel of block 1 may be calculated, such that the contours of the ultrasonic images corresponding to block 1 may be extracted.

In addition, the luminance values for each pixel are continuously added and accumulated while the difference image filter of the 3×3 pixels is applied to block 1.

The contour extraction is performed by applying the difference image filter of the 3×3 pixels to all the blocks divided up to the remaining blocks 2 to 25 according to the foregoing manner.

Further, step S130 is similarly applied to the ultrasonic images of 20 frames.

When the contour extraction of the ultrasonic images for each block is completed at step S130, each block is analyzed at the analyzing the block (S140) to calculate an average luminance value AVG_Lum_BL of each block.

Then, the average luminance value AVG_Lum_BL of each block is calculated by dividing the luminance value (for example, a total sum of pixel luminance of blocks) obtained by adding and accumulating the luminance values of each pixel for each block at the time of performing the contour extraction at step S130 into the total pixel number of the block, according to the following Equation 8.

$$AVG\_Lum\_BL = \text{Total sum of pixel luminance of block}/\text{Total pixel number of block} \quad (8)$$

The average luminance value AVG_Lum_BL of each block is calculated by applying Equation 8 to all of the divided blocks.

Thereafter, the average luminance value AVG_Lum_FRAME of all the frames is calculated by dividing the total sum of the average luminance value AVG_Lum_BL of each block by the total block number according to the following Equation 9.

$$AVG\_Lum\_FRAME = \text{Total sum of AVG\_Lum\_BL of each block/Total block number} \quad (9)$$

When the average luminance value AVG_Lum_BL of each block and the average luminance value AVG_Lum_Frame of all the frames are calculated at step S140, the optimal block number is determined for comparing with the average luminance values of the blocks of other frames and the corresponding optimal blocks are selected, at the determining and selecting the optimal block number (S150).

FIG. 4 is a graph of the optimal block number according to the average luminance value of the frame.

Referring to FIG. 4, the luminance value of the ultrasonic image is divided into 1 to 255 levels and the optimal block number to be compared with the optimal blocks of other frames is determined according to the average luminance value AVG_Lum_FRAME of the analyzed frame.

Determining the optimal block number is difficult to extract or identify the contours of the ultrasonic images when the ultrasonic image is too dark due to too small average luminance value AVG_Lum_FRAME or the ultrasonic of the analyzed frame is too bright due to too large average luminance value AVG_Lum_FRAME of the analyzed frame.

Therefore, when comparing the optimal blocks of the analyzed frame and the remaining frame, it is possible to more accurately estimate the acoustic velocity by comparing several optimal blocks than comparing only one optimal block of each frame.

However, it may take a long time when comparing a lot of optimal blocks in order to accurately estimate the acoustic velocity.

Therefore, in order to accurately and rapidly estimate the acoustic velocity, the optimal block number is determined for comparing with other frames by using the graph of the optimal block number according to the luminance value as shown in FIG. 4.

The optimal block number Block_Number is calculated by multiplying the average luminance value AVG_Lum_FRAME of the analyzed frame by coefficient K as represented by Equation 10.

$$Block\_Number = AVG\_Lum\_FRAME \times K \quad (10)$$

In Equation 10, K is any coefficient set by the user. K may be variably set according to the ultrasonic diagnosis apparatus.

In detail, when it is assumed that the ultrasonic image is the clearest in the default luminance region shown in FIG. 4, more optimal blocks are needed as the average luminance value AVG_Lum_FRAME of the analyzed frame is away from the default luminance regions.

For example, if two optimal blocks are needed in the default luminance region, 5 or less optimal blocks are needed, when the average luminance value AVG_Lum_Frame of the analyzed frame is in the range of 70 to 185 levels and 5 to 9 optimal blocks are needed when the average luminance value AVG_Lum_FRAME of the analyzed frame is in the range of 35 to 70 levels or 185 to 227 levels.

As such, when the optimal block number is determined according to the average luminance value AVG_Lum_FRAME of the analyzed frame, the optimal blocks for comparing with other frames is selected as many as the selected optimal block number in a to sequence of the largest value among the average luminance value AVG_Lum_BL of each block calculated in step S140.

For example, when the optimal block number is determined to be 3, 3 blocks are selected in a sequence of the largest value among average luminance value AVG_Lum_BL of each block calculated at step S140.

When the optimal block number is determined according to the average luminance value AVG_Lum_FRAME of the analyzed frame at step S150 and the corresponding optimal blocks are selected, the optimal frame is selected at the selecting the following optimal frame (S160) to estimate the acoustic velocity of the optimal frame as the real acoustic velocity of the ultrasonic image.

In detail, the frame corresponding to the blocks having the maximum luminance value is selected as the optimal frame by comparing blocks corresponding to the optimal blocks selected at step S150 for each frame to detect the optimal blocks having the maximum luminance value.

When the optimal frame is selected at step S160, the real acoustic velocity of the object of which the acoustic velocity of the optimal frame will be diagnosed at step S170 is estimated, which is applied to the ultrasonic diagnosis apparatus.

Meanwhile, the ultrasonic diagnosis apparatus using the method for estimating the acoustic velocity of the ultrasonic image as described above will be described below.

Figure 5:
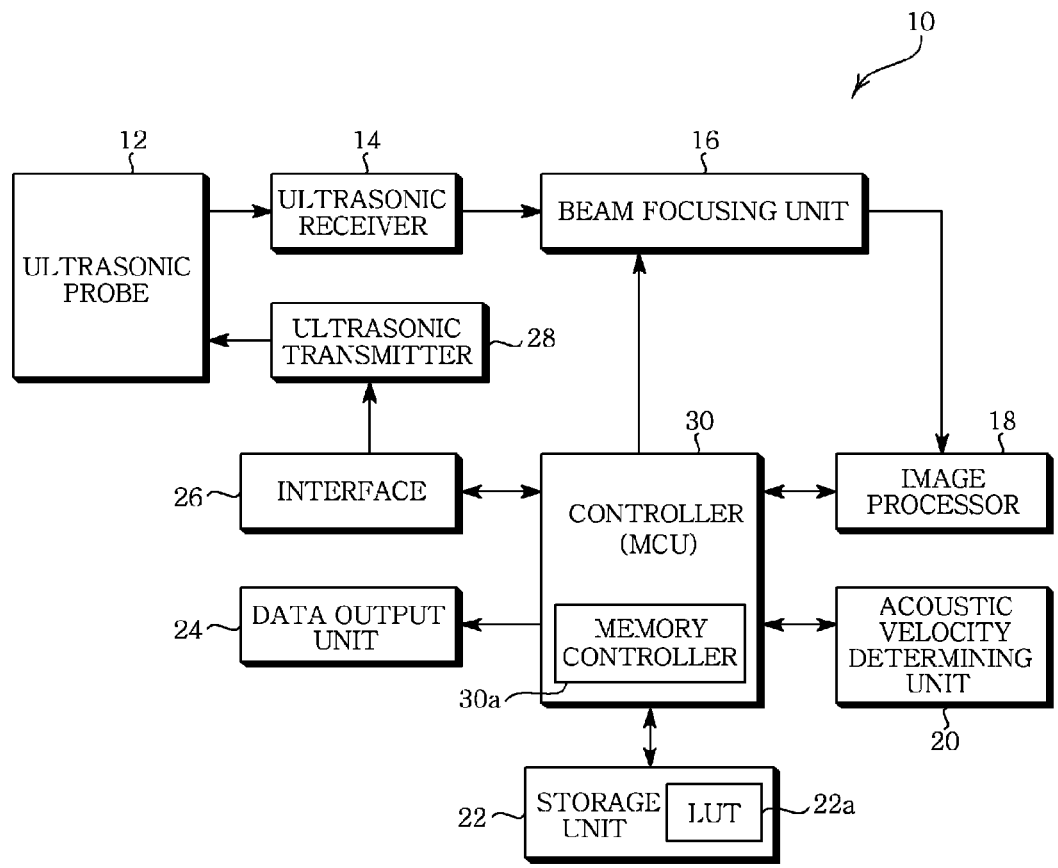
FIG. 5 is a block configuration diagram of an ultrasonic diagnosis apparatus according to an embodiment of the present invention.

FIG. 5 is a block configuration diagram of an ultrasonic diagnosis apparatus according to an embodiment of the present invention.

Referring to FIG. 5, an ultrasonic diagnosis apparatus 1 according to an embodiment of the present invention is configured to include an ultrasonic probe 12, an ultrasonic receiver 14, a beam focusing unit 16, an image processor 18, an acoustic determining unit 20, a storage unit 22, an interface 26, a data output unit 24, an ultrasonic transmitter 28, and a controller MCU 30.

The ultrasonic probe 12 emits the ultrasonic wave having a predetermined acoustic velocity into the human body of the subject and receives the ultrasonic wave (hereinafter, referred to as 'reflected wave') reflected from the tissue of the human body of the subject.

In detail, the ultrasonic probe 12 reflects, scatters, and transmits the ultrasonic wave transmitted therefrom depending on the various types of vehicles of the tissue of the human body when the ultrasonic wave contacts the tissue of the human body of the subject. At this time, the ultrasonic probe 12 receives the reflected wave returned by being returned from the tissue in the human body.

As such, in order to transmit and receive the ultrasonic wave into and from the human body of the subject through the ultrasonic probe 12, an ultrasonic transmitter 28 and an ultrasonic receiver 14 that converts ultrasonic waves into electric signals and electric signals into ultrasonic waves are needed.

The ultrasonic transmitter 28 generates the electric signals (hereinafter, referred to as 'transmitting signal') having a predetermined acoustic velocity according to a control signal from a controller 30 and converts the transmitting signals into the ultrasonic beam into ultrasonic beams to be emitted to the human body of the subject and transmits them to the ultrasonic probe 12.

The ultrasonic transmitter 28 is configured to include a transmitting beam former (not shown) that converts the transmitting signals into ultrasonic beams.

The transmitting signal is a transmitting signal having the preset acoustic velocity according to the control of the controller 30 or a transmitting signal having the optimal acoustic velocity determined by estimating the real acoustic velocity of the reflected wave.

The ultrasonic receiver 14 emits the ultrasonic beam generated from the ultrasonic transmitter 28 to the human body of the subject through the ultrasonic probe 12, receives the reflected waves from the tissue in the human body of the subject, and transfers them to the beam focusing unit 16.

The ultrasonic receiver 14 is configured to include a receiving beam former (not shown) that converts the reflected wave received from the ultrasonic probe 12 into the electric signals (hereinafter, referred to as 'received signal').

The beam focusing unit 16 focuses the received signals and transmits them to the image processor 18.

The image processor 18 generates and processes the ultrasonic images based on the received signals through the beam focusing unit 16.

Figure 6:
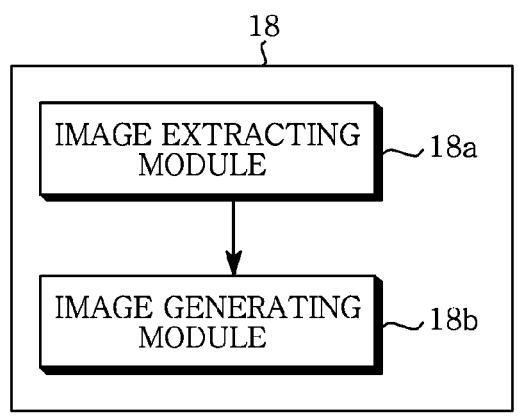
FIG. 6 is a detailed block configuration diagram of an image processor shown in FIG. 5.

FIG. 6 is a detailed block configuration diagram of an image processor shown in FIG. 5.

Referring to FIG. 6, the image processor 18 is configured to include an image extracting module 18a and an image generating module 18b.

The image extracting module 18a divides the received signal having the predetermined acoustic velocity focused from the beam focusing unit 16 into a plurality of received signals to extract each image signal.

For the convenience of explanation, in the present invention, it is assumed that the ultrasonic image signals of 20 frames are extracted from 20 received signals and the image generating module 18b generates the ultrasonic images of 20 frames based on 20 image signals extracted from the image extracting module 18a.

The generated ultrasonic images of 20 frames are stored in a storage unit 22 in a look-up table 22a through a memory controller 30a of the controller 30.

The acoustic velocity determining unit 20 uses the plurality of ultrasonic images to estimate the real acoustic velocity of the reflected wave from the tissue in the human body in real time and to determine the optimal acoustic velocity.

To this end, the acoustic velocity determining unit 20 is operated in two operating modes.

A first operating mode, which is an optimal block selecting mode, divides one of the ultrasonic images of multiple frames into a plurality of blocks to extract the contours of the ultrasonic images of each block and analyzes the luminance values of each block to determine the optimal block number, thereby selecting the optimal blocks.

The second operating mode, which is an optimal frame selecting mode, applies the optimal block position as the same as the optimal block position selected from the first operating mode to the remaining frame to compare the average luminance values of the optimal blocks of each frame, thereby finally selecting the frame corresponding to the optimal blocks having the maximum luminance values as the optimal frame.

The acoustic determining unit 20 estimates the acoustic velocity of the optimal frame finally selected by the first and second operating modes as the real acoustic velocity and applies it to the ultrasonic diagnosis apparatus 1 according to the present invention.

Figure 7:
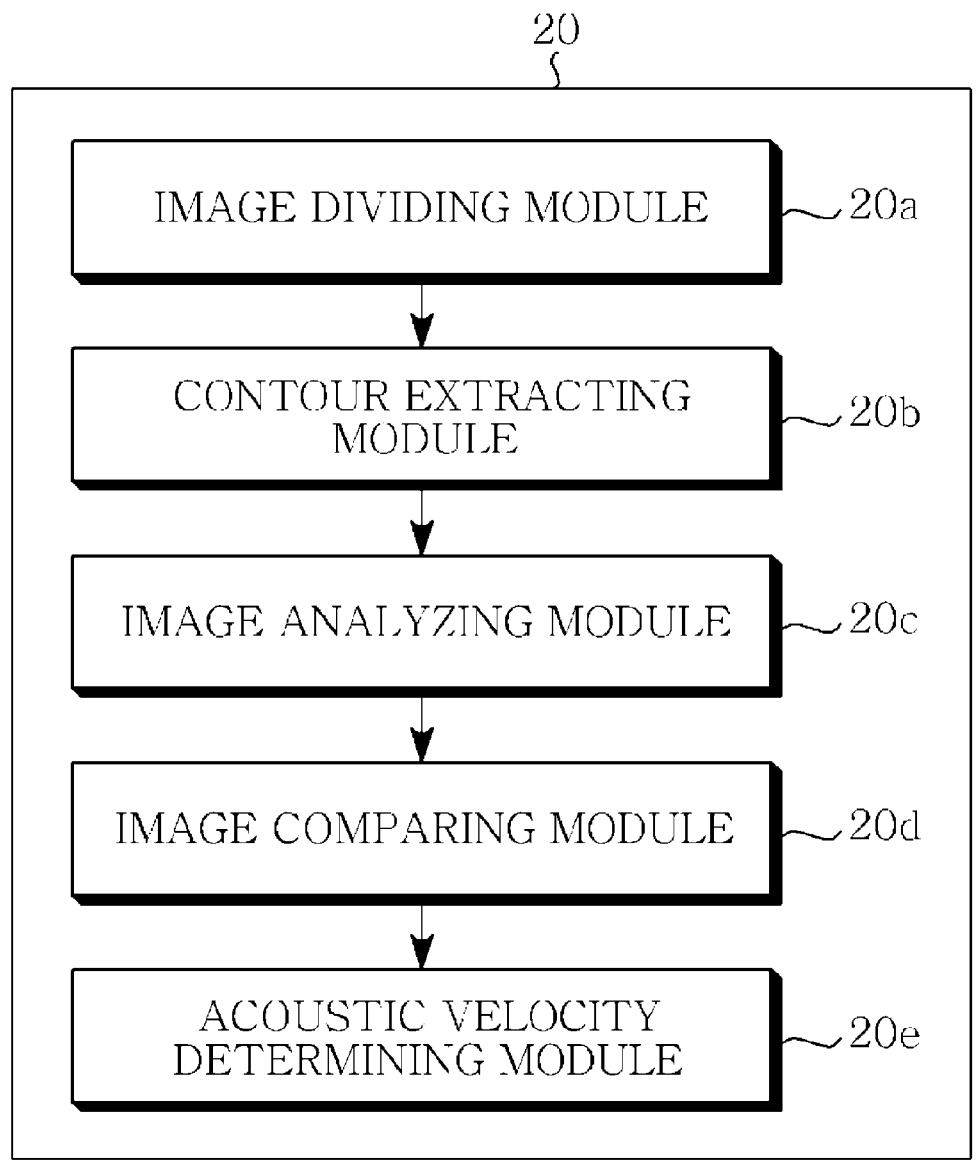
FIG. 7 is a detailed block configuration diagram of an acoustic velocity determining unit shown in FIG. 5.

FIG. 7 is a detailed block configuration diagram of an acoustic velocity determining unit shown in FIG. 5.

Referring to FIG. 7, the acoustic velocity determining unit 20 is configured to include an image dividing module 20a, a contour extracting module 20b, an image analyzing module 20c, an image comparing module 20d, and an acoustic velocity determining module 20e.

First, the operation of the above-mentioned components at the first operating mode will be described below.

The image dividing module 20a reads the ultrasonic images of 20 frames stored in the storage unit 22 and then, crops the required ultrasonic image portions, respectively.

During the cropping, the predetermined region may be set so that relevant images are manually cropped by the user or the images of a specific portion are automatically cropped.

Thereafter, the ultrasonic images of 20 frames, each of which is cropped, are divided into a plurality of blocks (for example, N×M) for each frame.

The contour extracting module 20b applies the difference image filter of the L×L pixels (for example, 3×3 pixels) to 25 blocks divided by the image division module 20a to calculate the luminance value for all the pixels of each block, thereby extracting the contours.

The image analyzing module 20c calculates the average luminance values AVG_Lum_BL of each block to digitize and analyze the ultrasonic images of each block when the contour extraction of each block is completed.

The average luminance values AVG_Lum_BL are calculated by dividing the total sum of the pixel luminance of each block by the total pixel number of each block and is stored in a lookup table 22a of the storage unit 22.

Thereby, the average luminance values AVG_Lum_BL of each block may be extracted in ascending order or descending order.

In addition, the average luminance value AVG_Lum_FRAME of the analyzed to frame is calculated by dividing the total sum of the average luminance values AVG_Lum_BL of each block of the analyzed frame by the total block number of the analyzed frame and is also stored in the lookup table 22a of the storage unit 22.

The image comparing module 20d determines the optimal block number by using the graph representing the optimal block number according to the average luminance value AVG_Lum_FRAME of the frame and determines the optimal block number to be compared with the block of the remaining frame according to the average luminance value AVG_Lum_Frame of the analyzed frame calculated in the image analyzing module 20c.

When the optimal block number is determined, the optimal blocks are selected as many as the optimal block number determined in a sequence of the largest value among the average luminance values AVG_Lum_BL of each block calculated in the image analyzing module 20c.

When the optimal blocks of the analyzed frame are selected by the above-mentioned process, the blocks having the maximum luminance value are extracted by comparing the optimal blocks at the same position even in the case of the remaining frame.

The acoustic velocity determining module 20e selects the frame corresponding to the blocks having the maximum luminance value extracted from the image comparing module 20d as the optimal frame and estimates the acoustic velocity of the optimal frame as the real acoustic velocity of the reflected wave from the diagnosis object and again applies it to the ultrasonic diagnosis apparatus 1 according to the present invention.

Referring back to FIG. 1, the storage unit 22 stores the ultrasonic images of the plurality of frames generated by the image processor 18 and the acoustic velocity determining unit 20, the average luminance value AVG_Lum_FRAME of each frame, the average luminance value AVG_Lum_BL of each block of frames, etc. In addition, the data are prepared in the form of the lookup table 22a, which may be stored in the storage unit 22.

The data output unit 24 estimates the real acoustic velocity according to the tissue of the human body in the acoustic velocity determining unit 20 in real time and outputs the ultrasonic images having the determined optimal acoustic velocity.

The interface 26 transfers the control signals to the ultrasonic transmitter 28 to according to the control of the controller 30.

Two control signals are transmitted to the ultrasonic transmitter 28 from the controller 30 through the interface 26.

One is a control signal to allow the ultrasonic transmitter 28 to generate the transmitting signals as the preset acoustic velocity in the controller 30 and the other is a control signal to allow the ultrasonic transmitter 28 to generate the transmitting signals as the optimal acoustic velocity determined from the acoustic velocity determining unit 20.

The controller 30 generally controls the ultrasonic diagnosis apparatus 1 according to an exemplary embodiment of the present invention.

The controller 30 generates the transmitting signals according to the control signal and converts them into the ultrasonic beams, thereby emitting the ultrasonic beams to the objects.

The controller 30 receives the reflected waves returned by reflecting the ultrasonic beam from the objects.

In addition, the controller 30 performs a control to divide and extract the received reflected wave into a predetermined unit (for example, 10 m/s) of the acoustic velocity thereof and converts them into the plurality of received signals and generate and store the ultrasonic images of the plurality of frames from the plurality of received signals.

Thereafter, the controller 30 performs a control determine the blocks as the same position of the optimal blocks as the optimal blocks of the plurality of frames to select the optimal frame and estimate the acoustic velocity of the optimal frame as the real acoustic velocity of the reflected waves to determine it as the optimal acoustic velocity, after selecting the optimal blocks from any one frame among the ultrasonic images of the plurality of frames.

As described above, the method for estimating the acoustic velocity of the ultrasonic images and the ultrasonic diagnosis apparatus using the same according to the exemplary embodiment of the present invention compares and provides only the predetermined optimal blocks in a sequence of the largest luminance value without comparing all the ultrasonic images in order to estimate the real acoustic velocity of the ultrasonic images, thereby to making it possible to estimate the acoustic velocity of the ultrasonic images in real time.

The present invention can more rapidly and accurately estimate the acoustic velocity by dividing the ultrasonic images and defining the analysis regions in the entire ultrasonic images.

In addition, the present invention can obtain higher-definition ultrasonic images by applying the estimated acoustic velocity to the ultrasonic diagnosis apparatus in real time.

Although the embodiments of the present invention has been disclosed for illustrative purposes, those skilled in the art will appreciate that various modifications, additions and substitutions are possible, without departing from the scope and spirit of the invention. Accordingly, such modifications, additions and substitutions should also be understood to fall within the scope of the present invention.

What is claimed is:

1. A method for estimating acoustic velocity of an ultrasonic image, comprising:
   (A) dividing each of the ultrasonic images of a plurality of input frames into a plurality of blocks;
   (B) extracting contours of the ultrasonic images corresponding to each of the plurality of blocks for each of the frames;
   (C) calculating and analyzing average luminance values of each of the blocks for each of the frames in order to select optimal blocks in a sequence of blocks having a maximum luminance value among average luminance values of each of the blocks when the contour extraction for each of the blocks is completed;
   (D) determining the number of optimal blocks according to the average luminance of each of the frames by calculating the average luminance values of each of the frames using the average luminance values of each analyzed block and selecting the optimal blocks as many as the number of optimal blocks; and
   (E) selecting, as an optimal frame, a frame corresponding to the optimal block having a maximum luminance value among the optimal blocks of each frame after comparing the selected optimal blocks with the optimal blocks of the remaining frames and estimating and applying acoustic velocity of the optimal frame as the real acoustic velocity,
   wherein step (D) includes:
   (D-1) calculating the average luminance values of each of the frames by using the average luminance values of each analyzed block,
   (D-2) determining the number of optimal blocks according to the average luminance values of the frames, and
   (D-3) selecting the optimal blocks as many as the number of optimal blocks in an order of the maximum luminance value among the average luminance values of each block.

2. The method for estimating acoustic velocity of an ultrasonic image as set forth in claim 1, wherein step (B) extracts the contours of the ultrasonic images of each block by applying a difference image filter to each block to calculate the luminance values of each pixel for each block.

3. The method for estimating acoustic velocity of an ultrasonic image as set forth in claim 2, wherein the difference image filter applied to each block calculates the absolute value of the difference of the luminance value between the pixels adjacent to one pixel to determine the maximum absolute value among the absolute values as the luminance value of the one pixel.

4. The method for estimating acoustic velocity of an ultrasonic image as set forth in claim 1, wherein step (C) calculates the average luminance values of each block by dividing the total sum of the luminance values of each pixel for each block by the total number of pixels of each block.

5. The method for estimating acoustic velocity of an ultrasonic image as set forth in claim 1, wherein step (D-1) calculates the average luminance values of each of the frames by dividing the total sum of the average luminance values of each of the analyzed blocks by the total number of blocks of each of the frames.

6. The method for estimating acoustic velocity of an ultrasonic image as set forth in claim 1, wherein step (E) includes:
   (E-1) comparing the selected optimal blocks with the optimal blocks of the remaining frames;
   (E-2) selecting the frame corresponding to the optimal blocks having the maximum luminance values among the optimal blocks of each frame as the optimal frame; and
   (E-3) estimating and applying the acoustic velocity of the optimal frame as the real acoustic velocity.

7. An ultrasonic diagnosis apparatus, comprising:

an ultrasonic transmitter that generates transmitting signals according to a control signal and converts the transmitting signals into ultrasonic beams;

an ultrasonic probe that emits the ultrasonic beams to objects and receives reflected waves returned from the objects;

an ultrasonic receiver that converts the reflected wave into electric signals to generate the received signals;

an image processor that divides and extracts the received signals into a plurality of acoustic velocities and generates the ultrasonic images of a plurality of frames;

an acoustic velocity determining unit that divides each of the ultrasonic images of the frames generated from the image processor into a plurality of blocks to extract contours, analyzes the luminance values of each of the blocks for each of the frames to determine the number of optimal blocks, and selects an optimal frame by selecting the optimal blocks as many as the number of optimal blocks and applying them to the remaining frames to estimate the acoustic velocity of the optimal frame as the real acoustic velocity of the reflected wave; and a controller that performs a control to generate an ultrasonic image control signal, generates the ultrasonic beam according to the control signal, and receives the reflected wave of the emitted ultrasonic beam to generate the ultrasonic images of the plurality of frames, divides each of the ultrasonic images of the frames into the plurality of blocks to extract contours, analyzes the luminance values of each of the blocks to determine the number of optimal blocks, and selects an optimal frame by selecting the optimal blocks as many as the number of optimal blocks and applying them to the remaining frames to estimate the acoustic velocity of the optimal frame as the real acoustic velocity of the reflected wave, wherein the acoustic velocity determining unit includes:

an image dividing module that divides the ultrasonic images of each of the frames generated from the image processor into the plurality of blocks, a contour extracting module that extracts the contours of the ultrasonic images of each of the blocks by applying the difference image filter to the ultrasonic images of each block of each of the plurality of frames to calculate the luminance values for each pixel of each block, an image analyzing module that calculates average luminance values of each block to digitize and analyze the ultrasonic images of each block, when the contour extraction of each block is completed, an image comparing module that determines the number of optimal blocks according to the average luminance value of the frames to select the optimal blocks as many as the number of optimal blocks in an order of the largest value among the average luminance values of each block and compares the optimal blocks of each frame by applying the positions of the optimal blocks to the remaining frames to select the optimal block having the maximum luminance value, and an acoustic velocity determining module that selects the frame corresponding to the optimal block having the maximum luminance value as the optimal frame to estimate the selected optimal frame as the real acoustic velocity of the reflected wave.

8. The ultrasonic diagnosis apparatus as set forth in claim 7, further comprising a data output unit outputting the ultrasonic images.

9. The ultrasonic diagnosis apparatus as set forth in claim 7, wherein the image processor includes:

an image extracting module that divides the received signals into the plurality of acoustic velocities to extract the plurality of image signals; and an image generating module that generates the ultrasonic images of the plurality of frames based on the plurality of images signals.

* * * * *